(12) United States Patent
Hughes et al.

(10) Patent No.: US 10,907,192 B2
(45) Date of Patent: Feb. 2, 2021

(54) SYSTEMS AND METHODS FOR ARTIFICIAL TEST STRIP CONTROLS

(71) Applicant: Polymer Technology Systems, Inc., Indianapolis, IN (US)

(72) Inventors: Gary L. Hughes, Camby, IN (US); Aniruddha Patwardhan, Fishers, IN (US); Keith Moskowitz, Indianapolis, IN (US)

(73) Assignee: POLYMER TECHNOLOGY SYSTEMS, INC., Whitestown, IN (US)

( * ) Notice: Subject to any disclaimer, the term of this patent is extended or adjusted under 35 U.S.C. 154(b) by 579 days.

(21) Appl. No.: 15/093,236

(22) Filed: Apr. 7, 2016

(65) Prior Publication Data

US 2016/0298170 A1 Oct. 13, 2016

Related U.S. Application Data

(60) Provisional application No. 62/144,233, filed on Apr. 7, 2015.

(51) Int. Cl.

| | |
|---|---|
| *C12Q 1/60* | (2006.01) |
| *G01N 21/78* | (2006.01) |
| *G01N 21/84* | (2006.01) |
| *G01N 33/52* | (2006.01) |
| *G01N 33/96* | (2006.01) |
| *G01N 21/77* | (2006.01) |

(52) U.S. Cl.
CPC ............... *C12Q 1/60* (2013.01); *G01N 21/78* (2013.01); *G01N 21/8483* (2013.01); *G01N 33/523* (2013.01); *G01N 33/96* (2013.01); *G01N 2021/7759* (2013.01); *G01N 2496/00* (2013.01)

(58) Field of Classification Search
CPC ............... G01N 21/8483; G01N 21/78; G01N 2021/7759; G01N 2496/00; G01N 33/523; G01N 33/96; C12Q 1/60
See application file for complete search history.

(56) References Cited

U.S. PATENT DOCUMENTS

| | | | | |
|---|---|---|---|---|
| 4,582,684 | A * | 4/1986 | Vogel | G01N 21/03 356/246 |
| 7,577,469 | B1 * | 8/2009 | Aronowitz | A61B 5/14532 600/310 |
| 2006/0231418 | A1 | 10/2006 | Harding et al. | |
| 2006/0237332 | A1 | 10/2006 | Hodges et al. | |
| 2011/0162978 | A1 * | 7/2011 | Cardosi | G01N 27/3274 205/777.5 |
| 2012/0234700 | A1 * | 9/2012 | Deng | A61B 5/14532 205/792 |

(Continued)

OTHER PUBLICATIONS

International Search Report dated Jul. 5, 2016 issued in related PCT App. No. PCT/US2016/26430 (2 pages).

(Continued)

*Primary Examiner* — Rebecca M Fritchman
(74) *Attorney, Agent, or Firm* — Haynes & Boone, LLP

(57) ABSTRACT

A linearity standard includes a plurality of calibration solutions, each calibration solution having a different level of a reactant having a known response in a test strip and meter combination, and an electronic storage medium for storing calibration instructions and known responses for each solution of the plurality of calibration solutions.

7 Claims, 6 Drawing Sheets

(56) References Cited

U.S. PATENT DOCUMENTS

2013/0295678 A1 11/2013 Riley et al.

OTHER PUBLICATIONS

PCT Written Opinion dated Jul. 5, 2016 issued in related PCT App. No. PCT/US2016/26430 (5 pages).
Coleiro, D, "Storage of Medicines and Medical Devices," 2012. Retrieved from the internet on May 29, 2016, https://www.um.edu.mt/_data/assets/pdf_file/0016/153160/Storage_of_Medicines_and_Medical_Devices.pdf.

* cited by examiner

ADVANTAGES:
- UNIQUE SETS FOR EACH CHEMISTRY
- APPEARANCE OF BIOLOGICAL ACTIVITY
- KITS OF CUSTOM STRIPS, MEMO CHIPS, PIPETTES

SYSTEMS AND METHODS FOR ARTIFICIAL TEST STRIP CONTROLS

CROSS-REFERENCE TO RELATED APPLICATIONS

This application claims the benefit of Provisional Application No. 62/144,233 filed on Apr. 7, 2015, titled "Systems And Methods For Artificial Test Strip Controls," the entire disclosure of which is hereby incorporated by reference.

BACKGROUND

Point-Of-Care ("POC") and home testing for various blood analytes and other detectable metrics in bodily fluids is desirable for both patients and doctors. In many scenarios, optical and electrochemical test strips are used for testing purposes. These test strips may approach the accuracy of laboratory tests; however, in some scenarios, they may not function properly. It is desirable to ensure that portions of the test strip are functioning properly. Additionally, it is desired to be able to isolate what portions of a test strip system are functioning properly and what portions are not.

BRIEF SUMMARY

In one embodiment, a system of linearity standards in a meter and a test strip combination includes a calibration solution and an electronic storage medium providing linearity standards for the test strip. Optionally, the calibration solution includes potassium ferricyanide. Alternatively, the meter and the test strip combination tests for total cholesterol. Optionally, the meter and test strip combination tests for one or more analytes selected from the list consisting of HDL cholesterol, LDL cholesterol, triglycerides, total cholesterol, glucose, creatinine, ketones, ALT, AST, and any other chemistry that relies on a peroxide-based trigger for a Trinder chemistry. Alternatively, the test strip includes a plurality of separation layers, and the calibration solution does not interact with the plurality of separation layers. In one alternative, the calibration solution only significantly interacts with chromophores of the test strip. In another alternative, the calibration solution includes a plurality of linearity controls. Alternatively, the solution is ferrocyanide, and a mediator in the test strip is potassium ferricyanide. Optionally, the calibration solution is ferricyanide, and a mediator in the test strip is potassium ferrocyanide. In another alternative, the calibration solution does not include serum. Optionally, the calibration solution is stable at room temperature.

In one embodiment, a method of using a meter and a test strip combination includes contacting the test strip with a calibration solution. The method further includes measuring a detectable property of the test strip with the meter. The method further includes adjusting the calibration of the meter for lots of test strips associated with the test strip based on the detectable property and an expected detectable property. Optionally, the calibration solution includes potassium ferricyanide. Alternatively, the meter and the test strip combination tests for total cholesterol. Optionally, the meter and test strip combination tests for one or more analytes selected from the list consisting of HDL cholesterol, LDL cholesterol, triglycerides, total cholesterol, and glucose. In one configuration, the test strip includes a plurality of separation layers, and the calibration solution does not interact with the plurality of separation layers. In another configuration, the calibration solution only significantly interacts with chromophores of the test strip. Optionally, the calibration solution includes a plurality of linearity controls. Alternatively, the calibration solution is ferrocyanide, and the meter is an electrochemical meter. Optionally, the calibration solution does not include serum. Alternatively, the calibration solution is stable at room temperature.

In another embodiment, a linearity standard includes a plurality of calibration solutions, each calibration solution having a different level of a reactant having a known response in a test strip and meter combination and an electronic storage medium storing calibration instructions and known responses for each solution of the plurality of calibration solutions. Optionally, the plurality of calibration solutions includes potassium ferricyanide. Alternatively, the meter and the test strip combination tests for total cholesterol. Optionally, the meter and test strip combination tests for one or more analytes selected from the list consisting of HDL cholesterol, LDL cholesterol, triglycerides, total cholesterol, and glucose. Alternatively, the test strip includes a plurality of separation layers, and the calibration solution does not interact with the plurality of separation layers. In one alternative, the calibration solution only significantly interacts with chromophores of the test strip.

DETAILED DESCRIPTION

Figure 1:
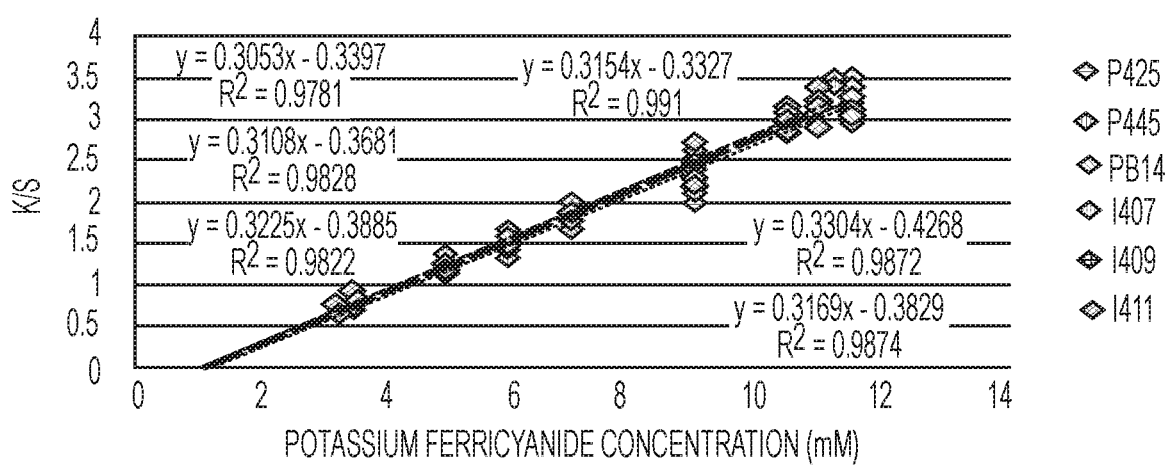
FIG. 1 shows results from using a potassium ferricyanide as a test strip control in a total cholesterol test strip.

Certain terminology is used herein for convenience only and is not to be taken as a limitation on the embodiments of the systems and methods for artificial test strip controls and linearity. In many scenarios, it is desirable to know that chromophores are functioning properly so that troubleshooting may be conducted for a test strip or test strip lot without testing actual samples or serum. The concentration of analytes in serum may be reliable; however, in many test strips, serum may act differently than whole blood, yielding inconsistent results. Additionally, certain test strips or meters may function properly at certain concentrations; however, they may not provide for a linear increase of measured analytes as analyte concentration is increased. Therefore, a test to confirm linearity is used in many scenarios.

It is desirable to have liquid linearity kits for all assays manufactured by PTS Diagnostics to make a linearity kit, and all the analytes being tested must be present in the solution. There can be stability issues with the linearity material. In addition, the serum-based material may behave differently on strips than whole blood because of the speed of the sample through the membranes. This is particularly observed with the PTS HDL assay, because the LDL fraction is not given time to precipitate. This HDL assay relies on a separation layer to separate out non-HDL cholesterol. If a sample containing all fractions of cholesterol flows too quickly through the separation layer, then the needed precipitation may not occur. This is an issue, since the final reaction layer reacts equally with LDL and HDL fractions.

In some embodiments, a solution is used that bypasses the enzyme reaction in the final layer that yields the color change or voltage, amperage, or other electrical activity change. In the case of reflectance assays, a potassium ferricyanide solution can be used to bypass an enzyme or enzyme cascades (enzyme trains) and react with the substrates that form a chromophore like in a Trinder chemistry reaction. For amperometric assays, a solution may be used to sidestep the enzymes and provide "free" electrons to the electrodes.

Such a system provides for many advantages, including:

(1) Artificial controls/linearity standards yield precise results because they are testing only the chromophore's response or current at the electrode. The imprecision from the enzyme reactions is eliminated.

(2) Artificial linearity standards act as a good optics check or amperometric instrument check to view linearity across the dynamic range of the test strip.

(3) Potassium ferricyanide testing on reflectance strips is very fast.

Specifically, using potassium ferricyanide is advantageous for colormetric reactions. Compared to plasma standards, there are many advantages, including:

(1) Potassium ferricyanide is relatively stable compared to standard linearity kits. It can be stored at room temperature; it just needs to be shielded from light.

(2) Artificial controls/linearity standards yield precise results because they are testing only the chromophore's response or current at the electrode. The imprecision from the enzyme reactions is eliminated.

(3) Artificial linearity standards act as a good optics check or amperometric instrument check to view linearity across the dynamic range of the test strip.

In many embodiments, a potassium ferricyanide solution may be an effective troubleshooting tool for optical test strips. Alternative substances may be used in electrochemical test strips. Since potassium ferricyanide only reacts with the chromophore used to produce a color change in the test strips, testing may be conducted on membrane checks (for monitoring consistent impregnation of chemistry across the length of the impregnated membrane) and failed lots to determine the root cause of the problem. If the color development is deemed good, then other diagnostic tools may be used to determine the root cause of the problem.

It is possible to use a series of potassium ferricyanide solutions to determine the linearity of an assay. Doing this type of linearity testing shows (1) the optics of a meter are working correctly and (2) the chromophore is stable. The following figures show the ferricyanide testing on several different lots. Notice that the color development is generally the same and linear. Not only can potassium ferricyanide solutions be used to test linearity, they also may be used as artificial controls. Again, it does not test the whole system but merely the meter's optics and the color reaction.

FIG. 1 shows various concentrations of potassium ferricyanide tested in a PTS total cholesterol test strip using an optical meter. As shown, the various test strips, Lipid Panel lots (P425, P445, PB14) and Chol+HDL+Glu panel lots (I407, I409, and I41) all deliver uniform and precise results at varying concentrations of potassium ferricyanide. The X-axis shows the concentration of potassium ferricyanide in mM and the Y-axis provides for the K/S (converting % Reflectance using the Kubelka-Munk expression) measurements. As is clear from the provided equations, the slot and intercepts of the equations are all very similar, and the $R^2$ for each trend line approaches one, showing that the data fits the trend lines well. It is thought that the color reaction portion for each test strip and the optical system was functioning normally in all cases. Therefore, it is clear how various concentrations of potassium ferricyanide could be used to test the function of test strips and optical meters.

Figure 2:
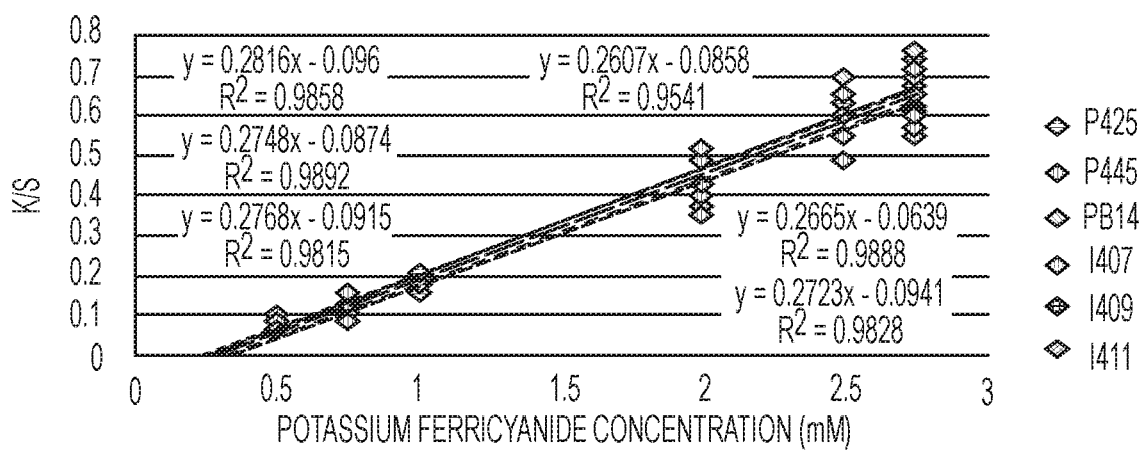
FIG. 2 shows results from using a potassium ferricyanide as a test strip control in an HDL test strip.

FIG. 2 shows various concentrations of potassium ferricyanide tested in a PTS HDL cholesterol test strip using an optical meter. As shown, the various test strips, P425, P445, PB14, I407, I409, and I411 all deliver uniform and precise results at varying concentrations of potassium ferricyanide. Similar to FIG. 1, precision is high, based on the expected results as well as the previous measurements, and the $R^2$ for each trend line approaches one.

Figure 3:
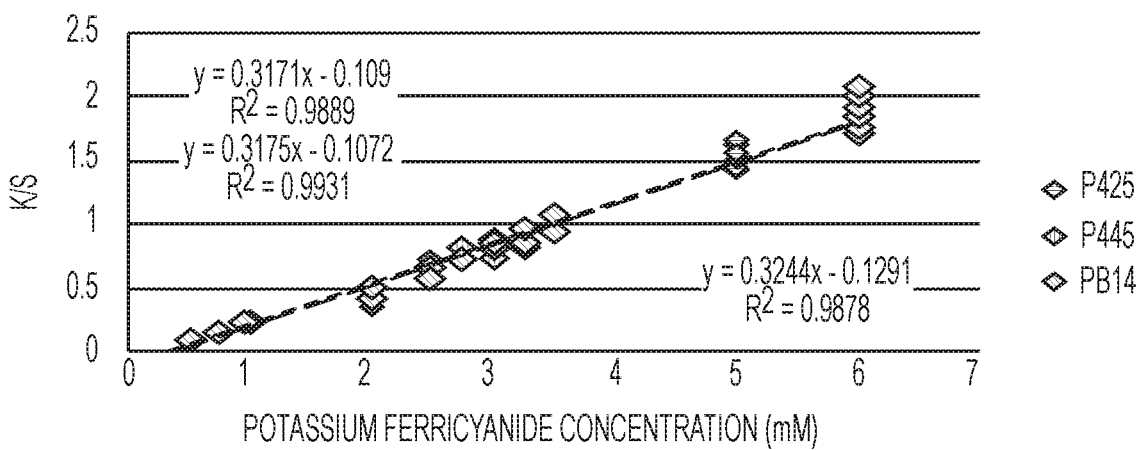
FIG. 3 shows results from using a potassium ferricyanide as a test strip control in a triglycerides test strip.
Figure 4A:
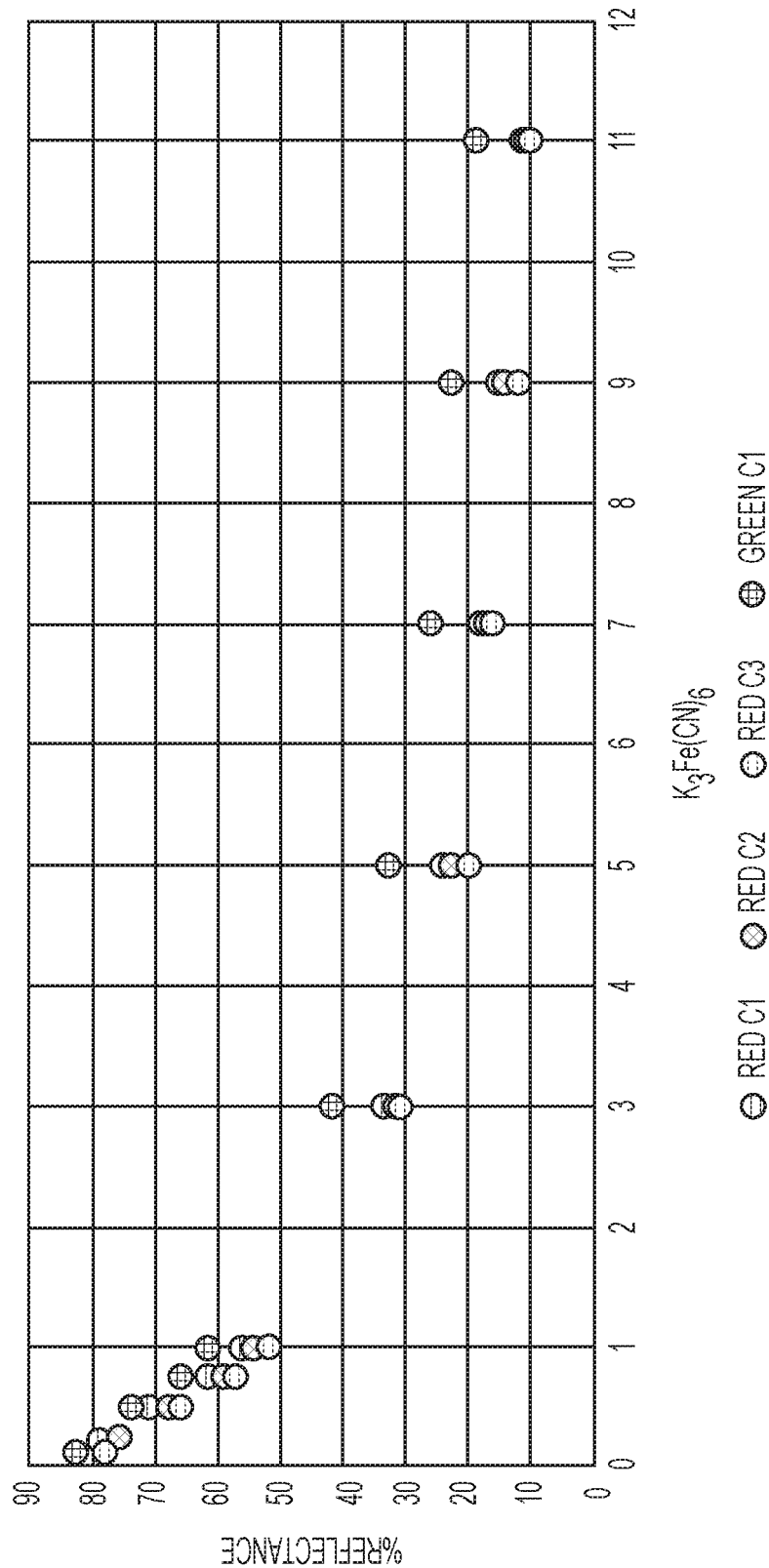
FIGS. 4A-4D show various results from linearity testing using potassium ferricyanide.
Figure 4B:
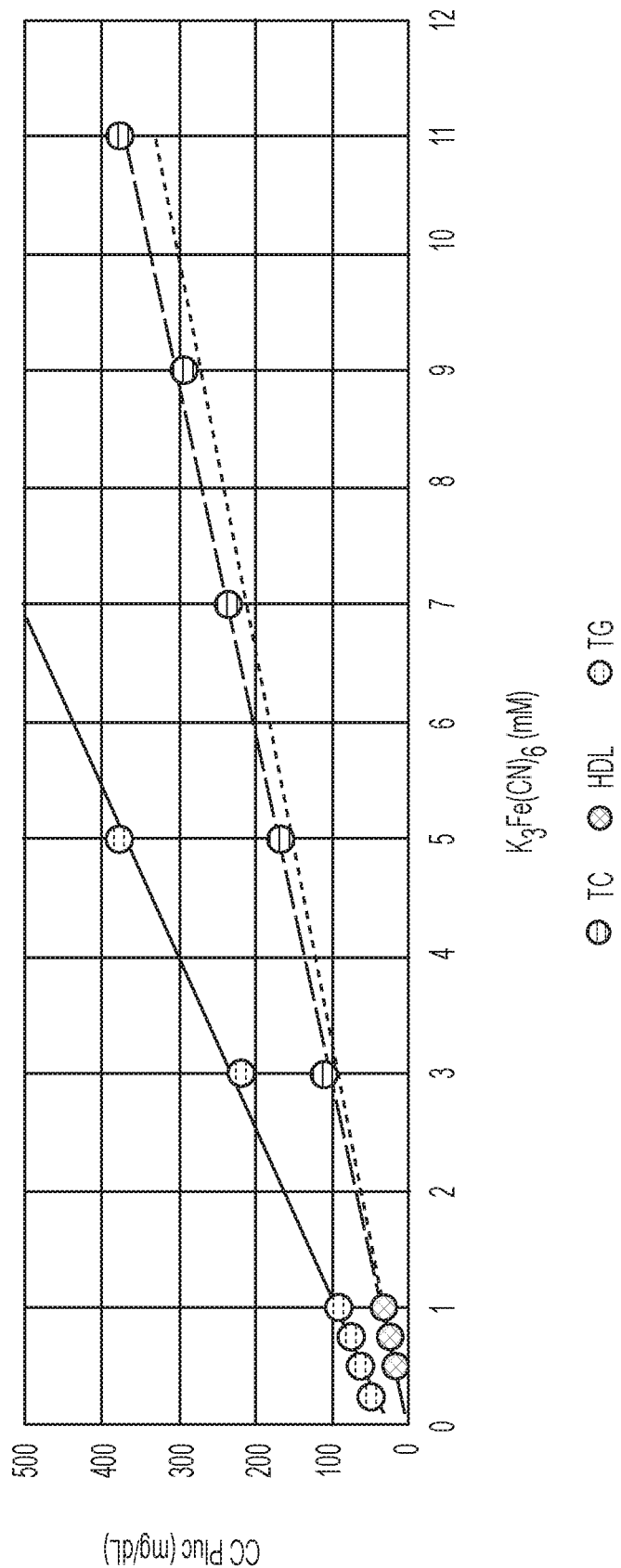
Figure 4C:
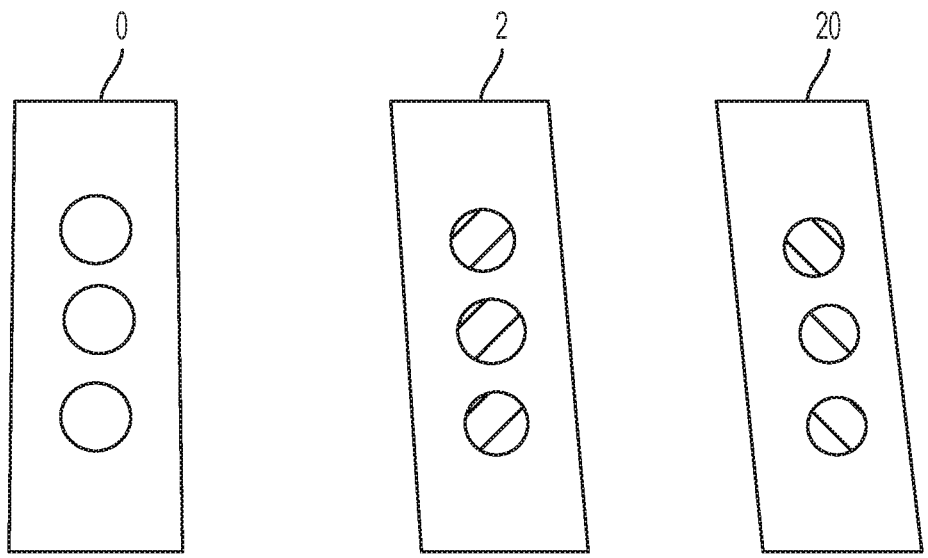
Figure 4D:
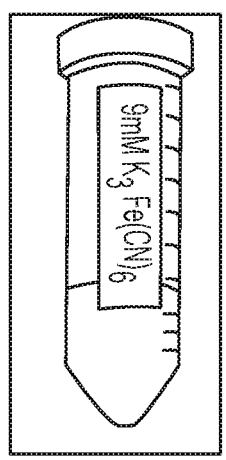

FIG. 3 shows various concentrations of potassium ferricyanide tested in a PTS triglycerides test strip using an optical meter. As shown, the various test strips, P425, P445, and PB14 all deliver uniform and precise results at varying concentrations of potassium ferricyanide. Similar to previous figures, precision is high based on the expected result as well as the previous measurements, and the $R^2$ for each trend line approaches one.

FIGS. 4A-4D show various results from linearity testing using potassium ferricyanide. Strips 410, 420, 430 show a photomicrograph of test strips treated with potassium ferricyanide. Strip 410 has been treated with a solution containing no potassium ferricyanide and shows no visible color change. Strip 420 has been treated with a solution containing 2 mM potassium ferricyanide and shows color change. Strip 430 has been treated with a solution containing 20 mM potassium ferricyanide and shows significant color change.

Graph 440 shows the relationship between reflectance and potassium ferricyanide concentration. An LED with approximately 670 nm wavelength is used. Each level of potassium ferricyanide gives similar reflectance values across the assays. Therefore, a linearity kit containing various samples at various concentrations of potassium ferricyanide may be provided.

Graph 460 shows results for a linearity kit using potassium ferricyanide with a PTS tri-panel test strip. The tri-panel test strip tests for total cholesterol, triglycerides, and HDL cholesterol. This shows the relationship between potassium ferricyanide and various analytes including total cholesterol, HDL, and triglycerides.

Figure 5:
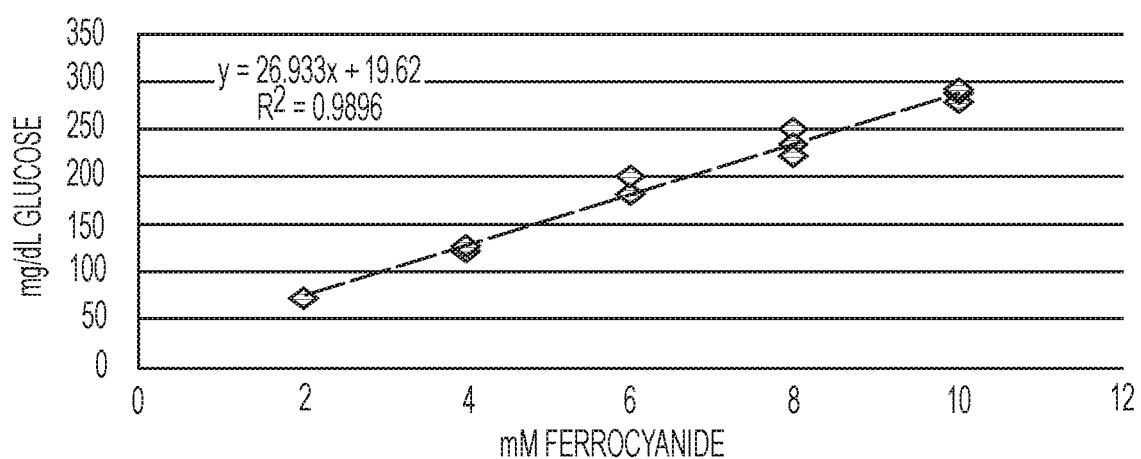
FIG. 5 shows results of using potassium ferrocyanide for electrochemical glucose analysis.

In addition to using potassium ferricyanide on reflectance-based assays as an artificial control or linearity standard, one can also use other artificial solutions for electrochemical tests. In many electrochemical tests, a voltage is applied to the reaction while the analyte is oxidized. The mediator is reduced into another form, and electrons are transferred to the electrode to measure current produced. Many electrochemical tests use ferricyanide as the mediator which is converted to ferrocyanide, reacting at the electrode. These tests can use ferrocyanide as an artificial control or linearity standard. In amperometric tests where ferricyanide is not the mediator, one can use a solution of the oxidized or reduced form of the mediator that reacts at the electrode. FIG. 5 shows the use of ferrocyanide as an artificial linearity standard for an amperometric glucose test.

The controls further may be provided with a MEMo chip or other electronic storage medium that provides for calibration information for the meter. During calibration procedures, the meter may calibrate the light or other signal (amperage) detected according to the expected detection values. Therefore, in many configurations, the controls may be provided with a MEMo chip or other electronic storage medium. The meter may be configured to run the calibration samples and ensure and adjust the calibration of the meters accordingly.

While specific embodiments have been described in detail in the foregoing detailed description and illustrated in the accompanying figures, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein, but is intended to cover modifications within the spirit and scope thereof as defined by the appended claims and any and all equivalents thereof. Note that, although particular embodiments are shown, features of each attachment may be interchanged between embodiments.

What is claimed as new and desired to be protected by Letters Patent of the United States is:

1. A method of calibrating a meter and a test strip combination, comprising:
    contacting the test strip with a calibration solution;
    measuring a detectable property of the test strip with the meter, the meter being an optical meter, wherein the detectable property is a first reflectance; and
    adjusting calibration of the meter for lots of test strips associated with the test strip based on the detectable property and an expected detectable property wherein the calibration solution includes potassium ferricyanide and the potassium ferricyanide reacts with a chromophore used in the test strip to produce a color change which is measured as the first reflectance, and the expected detectable property is a second reflectance corresponding to a reflectance expected from a concentration of the potassium ferricyanide in the calibration solution and wherein the potassium ferricyanide only reacts with the chromophore.

2. The method of claim 1, wherein the meter and the test strip combination tests for total cholesterol.

3. The method of claim 1, wherein the meter and test strip combination tests for one or more analytes selected from the list consisting of HDL cholesterol, LDL cholesterol, triglycerides, total cholesterol, and glucose.

4. The method of claim 1, wherein the test strip includes a plurality of separation layers, and the calibration solution does not interact with the plurality of separation layers.

5. The method of claim 1, wherein the calibration solution includes a plurality of linearity controls, the plurality of linearity controls including solutions containing different levels of potassium ferricyanide, such that generate different responses by the meter.

6. The method of claim 1, wherein the calibration solution does not include serum.

7. The method of claim 1, wherein the calibration solution is stable at room temperature.

* * * * *